United States Patent [19]

Thalhammer

[11] Patent Number: 5,591,859

[45] Date of Patent: Jan. 7, 1997

[54] PROCESS FOR THE PRODUCTION OF 2-CYANOIMINOTHIAZOLIDINE

[75] Inventor: Franz Thalhammer, Trostberg, Germany

[73] Assignee: SKW Trostberg Aktiengesellschaft, Trostberg, Germany

[21] Appl. No.: 509,740

[22] Filed: Aug. 1, 1995

[30] Foreign Application Priority Data

Aug. 4, 1994 [DE] Germany .......................... 44 27 539.0

[51] Int. Cl.[6] .............................................. C07D 277/18
[52] U.S. Cl. ................................................... 548/198
[58] Field of Search ........................................... 548/198

[56] References Cited

U.S. PATENT DOCUMENTS 5,532,258  7/1996  Katsura et al. .................... 548/198

FOREIGN PATENT DOCUMENTS 2205745  8/1973  Germany .

OTHER PUBLICATIONS

Org. Prep. Proced. Ind., Bd. 23, Nr. 6, 1991, pp. 721–728, XP002002935 Zmitek, J. et al.: "The Synthesis and Reactions of N–Cayno–O–methylpseudoureas" *Beispiel 7A*.

J. Heterocycl. Chem., Bd. 24, Nr. 1, 1987, pp. 275–278, XP002002936 Webb, R., W. Et Al.: "Diphenyl Cayncarbonimidate and Dichlorodiphenoxymethane as Synthones for the Construction of Heterocyclic Systems of Medical Interest".

J. Med. Chem., Bd. 38, No. 17, 1995, pp. 3236–3245, XP002002937 Atwal, K., S. et al.: "Cardioselective Anti–Ischemic ATP–Sensitive Potassium Chanel Openers. 3. Stucuture–Activity Studies on Benzopyranyl Cyanoguanidines: Modification of the Cyanoguanidine Portion".

*Primary Examiner*—Johann Richter
*Assistant Examiner*—John Peabody
*Attorney, Agent, or Firm*—Felfe & Lynch

[57] ABSTRACT

A process for the production of 2-cyanoiminothiazolidine by reaction of 2-aminoethanethiol (cysteamine) with a dialkyl-N-cyanoimidocarbonate.

21 Claims, No Drawings

PROCESS FOR THE PRODUCTION OF 2-CYANOIMINOTHIAZOLIDINE

BACKGROUND OF THE INVENTION

The present invention is in a process for the production of 2-cyanoiminothiazolidine by reacting 2-aminoethanethiol (cysteamine) with a dialkyl-N-cyanoimidocarbonate.

The synthesis of 2-cyanoiminothiazolidine using 2-aminoethanethiol is known. Thus the German laid-open specification DE 22 05 745 describes new heterocyclics substituted by a N-cyanoimino residue and processes for their production and inter alia the reaction of 2-aminoethanethiol with dialkyl-N-cyanoimido-dithiocarbonates. However, this process has the serious disadvantage that mercaptans are released during the reaction in twice the stoichiometric amount which are extremely difficult and time-consuming to handle because of their toxicity and their foul odor.

R. L. Webb et al., in J. Heterocycl. Chem. 24, 275, 1987 describe the use of diphenyl-N-cyanoimidocarbonate to produce 2-cyanoiminothiazolidine. Since diphenyl-N-cyanoimidocarbonate is not available in large amounts as a starting compound and the complete separation of the phenol released during the reaction from the reaction product is very time consuming, this process is unsuitable for an industrial production of 2-cyanoiminothiazolidine.

The production of 2-cyanoiminothiazolidine by reacting 2-aminoethanethiol with dimethyl-N-cyanoimidocarbonate in aqueous solution was described by I. Zmitek et al., in Org. Prep. Proced. Ind. 23, 721, (1991). However, the long reaction time and the small yield of 48% obtained in this way, render this process uneconomical. In addition, the physical data presented therein raises doubts as to whether the isolated and described product really is 2-cyanoiminothiazolidine.

THE INVENTION

The object of the present invention is therefore to provide a process for the production of 2-cyanoiminothiazolidine which can be carried out on an industrial scale and which takes into account environmentally-relevant aspects and leads to economically-acceptable yields and which avoids the aforementioned drawbacks of the state of the art.

This object is achieved according to the invention by a process for the production of 2-cyanoiminothiazolidine of formula

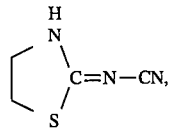

by reacting 2-aminoethanethiol and a dialkyl-N-cyanoimidocarbonate of the general formula

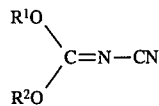

in which the residues $R^1$ and $R^2$ can be the same or different and represent aliphatic residues with 1 to 4 carbon atoms which together can also form an alkylene bridge. In the process of the invention a) start 2-aminoethanethiol and dialkyl-N-cyanoimidocarbonate are allowed to react for 30 minutes to 6 hours at temperatures between $-10°$ and $+40°$ C. in a pH range between 7 and 12 in water and/or an organic solvent and b) the reaction is completed at a pH value of $>8$ by an increase in temperature of $30°$ to $60°$ C.

It has turned out that the product 2-cyanoiminothiazolidine can be produced in surprisingly high yields and with unexpectedly high purity by this two-step process.

In the process according to the invention 2-aminoethanethiol (cysteamine) is first dissolved in water or a mixture of water and an organic solvent in which alcohols with 1 to 4 carbon atoms such as methanol and ethanol or acetone are used as the organic solvent. In an alternative variant according to the invention a salt of 2-aminoethanethiol can also be added first; the free cysteamine is then released from its salt form by addition of a base, such as sodium hydroxide solution, in an equimolar amount or in a slight excess, 2-aminoethanethiol hydrochloride being preferred for this. The concentration of the solution of the 2-aminoethanethiol is not usually a critical process parameter and thus can be varied within wide limits. A 1 to 4 molar solution is preferably added first. The molar ratio of 2-aminoethanethiol to dialkyl-N-cyanoimidocarbonate is advantageously 0.8 to 1.2:1, preferably about 1:1.

Dialkyl-N-cyanoimidocarbonate is then added to this solution in portions or continuously in a solid or dissolved form, dimethyl-N-cyanoimidocarbonate being preferably used.

The order in which the reaction partners are added is not limiting and can be varied as desired i.e. 2-aminoethanethiol can also be added to a solution of dialkyl-N-cyanoimidocarbonate which is already present according to another embodiment of the process according to the invention.

One of the essential features of the invention is that the actual reaction proceeds in two consecutive steps, in which firstly in reaction step a) the starting compounds 2-aminoethanethiol and dialkyl-N-cyanoimidocarbonate are reacted at temperatures between $-10°$ C. and $+40°$ C. In this process the dosage rate of dialkyl-N-cyanoimidocarbonate is regulated so that the temperature of the reaction mixture remains within the given range if necessary while cooling externally and is preferably between $+10°$ C. and $+25°$ C. In this procedure the duration of the dosing is usually about 15 to 30 minutes. It has proven to be advantageous for the process in general to carry out reaction step a) and also reaction step b) under an inert gas atmosphere.

After mixing the starting compounds they are stirred at the set temperature during a preferred reaction period of 2 to 4 hours during which a colorless suspension of the primary adduct forms. After this period the pH value of the solution, which is in a range of 7 to 12 during reaction step a), is adjusted to $>8$ in reaction step b) by addition of a base. Alkali hydroxides, alkali carbonates and strongly basic amines such as triethylamine and dimethylamine are preferred. In a particularly preferred variant these bases are added in an aqueous solution. The molar ratio of the added base and 2-aminoethanethiol is advantageously 0.05 to 1:1, and is preferably 0.1 to 0.2:1.

After the increase in temperature in reaction step b) of $30°$ to $60°$ which is essential according to the invention, the reaction mixture is stirred until the primary adduct can no longer be analytically detected and the formation of the thiazolidine ring is complete. The duration of the stirring process in this case depends on the reaction temperature which is preferably $40°$ to $50°$ C. higher than in reaction step a); thus usually 3 to 4 hours at $50°$ C. and 1.5 to 2 hours at $80°$ C. are usually required until the primary adduct has completely reacted.

Subsequently the pH value of the reaction mixture is brought into a neutral to acidic range by addition of acid, preferably hydrochloric acid. A slightly acidic pH value of about pH 6 has proven to be optimal since under these conditions the solubility of the product passes through a minimum and thus a colorless suspension is obtained.

In order to complete the product separation by crystallization, it can if necessary be cooled to a temperature of <20° C., in which case if a very dilute solution is present, an additional concentration step is recommended.

The suspension obtained in this manner is separated according to known methods such as filtration and the product obtained is washed with water or a water/alcohol mixture if necessary. Subsequently the moist product can be dried. Drying at temperatures of 50° to 90° C. having proven to be suitable.

2-Cyanoiminothiazolidine is obtained with the aid of the process according to the invention in yields of >65%, preferably >70% and most preferably >85% in the form of a pure white crystalline powder of high purity.

The process according to the invention is elucidated in more detail by the following examples.

EXAMPLE 1

11.6 g (0.1 mol) 2- aminoethanethiolhydrochloride was dissolved in 50 ml water in a stirring flask under a nitrogen atmosphere and 16.0 g (0.1 mol) of a 25% (w/w) sodium hydroxide solution was added within 10 minutes to this solution at temperatures between 10° and 20° C. After this solution had been stirred for a further 30 minutes at 20° C., 11.6 g (0.1 mol) dimethyl-N-cyanoimidocarbonate was subsequently added in portions. During this the temperature was kept at ca. 20° C. by external cooling and stirred for an additional 2.5 hours. The suspension which formed was then admixed with 2.0 g (0.02 mol) triethylamine and the temperature was increased to 50° C. After stirring for 3 hours at this temperature, the pH value was adjusted to 6 with 20% (w/w) hydrochloric acid and the suspension obtained was subsequently cooled to 10° C. The colorless solid is separated by means of a nutsch filter and washed twice with 10 ml water each time. After drying at 50° C. in a vacuum, 9.9 g (78% of theory) of a colorless crystalline powder was obtained the melting point of which was 153°–155° C.

A degree of purity of 99.9% was determined by means of HPLC. A further 1.0 g of the product can be isolated from the mother liquor by evaporation. Thus a total yield of 86% of theory is obtained.

EXAMPLE 2

11.6 g (0.1 mol) 2-aminoethanethiolhydrochloride was dissolved in 50 ml water under nitrogen and within 10 minutes 16.0 g (0.1 mol) of a 25% (w/w) sodium hydroxide solution was added. A solution of 14.2 g (0.1 mol) diethyl-N-cyanoimidocarbonate and 20 ml ethanol was added dropwise to this solution at 20° C. and the suspension that forms was stirred for 3 hours. After addition of 2.0 g (0.02 mol) triethylamine, it was heated for 4 hours to 60° C. Subsequently the pH value was adjusted to 6.5 with 20% (w/w) hydrochloric acid and it was cooled to 10° C. The precipitated solid was suction filtered, washed twice with 10 ml water each time and dried.

8.7 g (69% theory) product was obtained in this way with a melting point of 151°–153° C. and a purity of 99.1%.

EXAMPLE 3

7.8 g (0.1 mol) 2-aminoethanethiol in 50 ml water was admixed with 11.6 g (0.1 mol) dimethyl-N-cyanoimidocarbonate and stirred for 2.5 hours at 20° C. Afterwards 2.8 g (0.02 mol) potassium carbonate was added and the suspension was heated for 2 hours to 80° C.

After cooling to 10° C., the pH value was adjusted to 5 with hydrochloric acid, the precipitated solid was suction filtered and dried.

8.9 g (70% of theory) of 2-cyanoiminothiazolidine was obtained with a melting point of 150°–152° C. and a purity of 99.0%.

EXAMPLE 4

11.6 g (0.1 mol) 2-aminoethanethiolhydrochloride in 25 ml water was admixed under a nitrogen atmosphere with 16.0 g (0.1 mol) of a 25% (w/w) sodium hydroxide solution at a temperature below 20° C. and the solution that is formed is added dropwise at 20° C. to a prepared solution of 11.6 g (0.1 mol) dimethyl-N-cyanoimidocarbonate in water. Subsequently it was stirred for a further 2 hours and the suspension was admixed with 1.5 g (0.02 mol) of a 60% (w/w) solution of dimethylamine in water. After addition of the amine, the temperature was increased for 3 hours to 50° C. It was cooled and the pH value was adjusted to 5 with aqueous hydrochloric acid. The suspension was stirred for a further one hour at 10° C., the solid was separated by filtration and washed twice with 10 ml water.

After drying at 50° C. in a vacuum, 9.2 g (72% of theory) of 2-cyanoiminothiazolidine with a melting point of 153°–154° C. and a purity of 99.3% according to HPLC was obtained.

It will be understood that the specification and examples are illustrative but not limitative of the present invention and that other embodiments within the spirit and scope of the invention will suggest themselves to those skilled in the art.

I claim:

1. A process for the production of 2-cyanoiminothiazolidine of formula

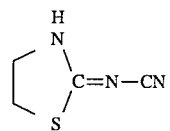

comprising, a) reacting 2-aminoethanethiol and a dialkyl-N-cyanoimidocarbonate of the general formula

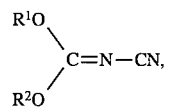

in which the residues $R^1$ and $R^2$ are the same or different and represent aliphatic residues with 1 to 4 carbon atoms which together can also form an alkylene bridge, for 30 minutes to 6 hours at a temperature of from −10° to +40° C. in a pH range from 7 to 12 in water and/or an organic solvent and b) the reaction is completed at a pH value of >8 by increasing the temperature by 30° to 60° C.

2. The process of claim 1, wherein $R^1$ and $R^2$ each represent a methylene residue.

3. The process of claim 1, wherein the organic solvent is an alcohol with 1 to 4 carbon atoms or acetone.

4. The process of claim 1, wherein the molar ratio of 2-aminoethanethiol to dialkyl-N-cyanoimidocarbonate is 0.8 to 1.2:1.

5. The process of claim 1, wherein the 2-aminoethanethiol is released from one of its salts by addition of a base before the reaction with the dialkyl-N-cyanoimidocarbonate.

6. The process of claim 5, wherein the salt is a hydrochloride.

7. The process of claim 6, wherein the base is added in an equimolar amount or in a slight excess.

8. The process of claim 5, wherein sodium hydroxide solution is added as the base.

9. The process of claim 1, the temperature in reaction step a) is between +10° and +25° C.

10. The process of claim 1, wherein the reaction period in reaction step a) is 2 to 4 hours.

11. The process of claim 1, wherein the pH value in reaction step b) is adjusted to >8 by addition of a base.

12. The process of claim 11, wherein alkali hydroxides, alkali carbonates or strongly basic amines in aqueous solution are used as the base in reaction step b).

13. The process of claim 12, wherein the base is at least one of triethylamine and di-ethylamine.

14. The process of claim 12, wherein the molar ratio of added base to 2-aminoethanethiol used is 0.05 to 1:1.

15. The process of claim 14, wherein the molar ratio is 0.1 to 0.2:1.

16. The process of claim 1, wherein the temperature in reaction step b) is increased by 40° to 50° C.

17. The process of claim 1, wherein the product is precipitated in a neutral to acidic pH range.

18. The process of claim 17, wherein the product is precipitated at pH 6.

19. The process of claim 1, wherein the product is separated by crystallization at a temperature of <20° C.

20. The process of claim 1, wherein reaction steps a) and b) are carried out under an inert gas atmosphere.

21. The process of claim 1 wherein the molar ratio of 2-aminoethanethiol to dialkyl-N-cyanoimidocarbonate is about 1:1.

* * * * *